US00PP19639P2

(12) United States Plant Patent
Friday

(10) Patent No.: US PP19,639 P2
(45) Date of Patent: Jan. 20, 2009

(54) PEACH TREE NAMED 'P.F. BIG GEORGE'

(50) Latin Name: *Prunus persica*
Varietal Denomination: P.F. Big George

(76) Inventor: Paul Friday, P.O. Box 850, Coloma, MI (US) 49038

( * ) Notice: Subject to any disclaimer, the term of this patent is extended or adjusted under 35 U.S.C. 154(b) by 43 days.

(21) Appl. No.: 11/807,889

(22) Filed: May 31, 2007

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent L Bell

(57) ABSTRACT

A new and distinct variety of peach, *Prunus persica,* tree having the following unique combination of desirable features:

1. The new and distinct variety of peach tree is of average height and of upright growth and a regular and productive bearer of peaches;
2. Producing a very firm fruit having a resilient flesh texture;
3. Blossoms are showy when in full bloom;
4. A substantially spherical fruit with skin of red color (50–80%) overlying yellow at the maturity of the fruit;
5. Very late maturing fruit of good taste; and
6. A very late maturing fruit of good storage and shelf life.

1 Drawing Sheet

Botanical classification: *Prunus persica.*

ORIGIN OF VARIETY

The new peach tree (hereinafter referred to as the 'P.F. Big George') was originated by Paul Friday in the experimental orchard, which is maintained for the purposes of breeding peach trees, located in Coloma, Mich. Coloma is located in the southwest section of Michigan, USDA Hardiness Zone 6A, with observed temperature ranges of minus 12 degree Fahrenheit to 90 degree Fahrenheit, also with annual rainfall of about 40 inches.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for there adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. Big George', was a single plant from one such seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard located in Coloma, Mich. The asexual propagation demonstrates that such reproduction of the characteristics of the tree are consistent and are established and transmitted through succeeding asexual propagation.

SUMMARY OF THE VARIETY

The new and very distinct variety of peach tree is of average height and of upright growth and a regular and productive bearer of peaches. A distinguishing characteristic is that it is a very late maturing peach, 54 days after 'Redhaven' (non-patented) in southwest Michigan. The blossoms are characterized as being showy. More specifically the blossoms of 'P.F. Big George' peach tree have angularly spaced five-blossom petals projecting upwardly at an inclined angle so as to form a blossom, having about 1½" diameter, measured across the blossoms. As the typical showy blossom as exemplified by 'Loring' (non-patented) peach.

The fruit at maturity is large, having flesh that is firm and a light yellow with red around the pit.

The skin is smooth having moderate to little down and is of dark red overlying yellow ground color. The yellow background covers approximately twelve percent (12%) of its surface at maturity. At maturity, the peach is spherical having an average diameter of about 2¾".

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of the market class. Thus, fruit of this tree remains more attractive to the ultimate buyer, the consumer, and thereby will command premium prices for late fresh desert market.

The fruit matures very late 54 days after 'Redhaven' (non-patented) peach in southwestern Michigan, it stores very well in a refrigerated room at 33 degree Fahrenheit for up to 3 weeks without becoming dry or mealy, remaining very sweet 15 brix of sugar. The fruit as mentioned heretofore is of dark red overlying yellow which covers approximately twelve percent (12%) of its surface and has a very attractive appearance.

BRIEF DESCRIPTION OF THE PHOTOGRAPHS

In the accompanying drawing the top photograph shows the leaves of the plant depicting both upper and lower sides. A tape measure is included showing the length of a leaf.

The bottom photograph shows two (2) whole fruits with one bisected across the axis showing that it is freestone, and has a clear yellow flesh with red around the pit. A tape measure has been placed in the photograph showing that the fruit form this tree has the genetic capability to exceed two and three-quarters inches (2¾") in diameter.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. Big George'.

Tree:
- *Age.*—Five (5) years.
- *Height.*—Unpruned 12'.
- *Width.*—Unpruned 8'.
- *Size.*—Medium.
- *Vigor.*—Vigorous.
- *Density.*—Medium — moderate pruning required.
- *Form.*—Upright.
- *Production.*—Very good — sizes well with a minimum amount of thinning.
- *Bearer.*—Consistent.
- *Disease resistance to bacterial leaf spot and fruit spot.*—Very resistant.
- *Rootstock.*—Grown on its own roots.

Trunk:
- *Bark.*—Gray (Pantone #437).
- *Size.*—Medium.
- *Surface.*—Semi-smooth.
- *Diameter.*—2½" diameter at 18" above ground at 5 years of age.
- *Lenticels.*—Semi-pronounced.
- *Lenticels size.*—⅛".

Branches:
- *Size.*—1½" diameter at 6" from trunk.
- *Surface.*—Semi-smooth.
- *Lenticels per square inch.*—Seventeen (17).
- *Lenticels color.*—(Pantone #172).
- *Lenticels size.*—1/16".
- *Crotch angles.*—45 degree angles.
- *Branch color.*—Gray (Pantone #436).
- *Internode length.*—½".

Leaves:
- *Size.*—Average length 8", Average width 2".
- *Form.*—Lanceolate — pointed.
- *Thickness.*—Medium.
- *Margin.*—Smooth.
- *Leaf base shape.*—Acute.
- *Leaf apex shape.*—Pointed.
- *Petiole length.*—½".
- *Gland shape.*—Oval.
- *Gland color.*—Brown.
- *Gland number.*—2 on each side of petiole.
- *Leaf color.*—Adaxial (Top) or upper leaf surface green (pantone#371).
- *Leaf color.*—Abaxial (Bottom) or bottom leaf surface (pantone #378).

Flowerbuds:
- *Size.*—⅜" long — ¼" wide.
- *Bud shape.*—Ovate.

Flowers:
- *Blooming period.*—Apr. 18, 2006 to Apr. 24, 2006.
- *Bloom size.*—1½" diameter.
- *Bloom depth.*—7/16" deep.
- *Size of petals.*—¾" long — ⅝" wide.
- *Shape of petals.*—Ovate.
- *Petal margins.*—Entire (smooth).
- *Petal base shape.*—Pointed.
- *Petal apex shape.*—Ovate.
- *Petal color.*—Top — pink (pantone#218), Bottom — pink (pantone#218).
- *Number of petals.*—Five (5).
- *Sepal size.*—¼" long — 3/16" wide.
- *Sepal shape.*—Ovate.
- *Sepal apex.*—Pointed.
- *Sepal base.*—Flat.
- *Sepal color.*—Pantone #216.
- *Number of sepals.*—Five (5).
- *Number of anthers.*—Sixteen (16).
- *Anthers color.*—Pantone #146.
- *Number of stamens.*—Sixteen (16).
- *Stamen length.*—7/16".
- *Stamen color.*—Pantone #215.
- *Pistil length.*—7/16".
- *Pistil color.*—Pantone #103.
- *Pollen.*—Self-pollinating.
- *Flower color.*—Pink Pantone #218.
- *Number flowers per cluster.*—Two (2).
- *Fragrance.*—Very fragrant.

Fruit:
- *Maturity when described.*—Firm ripe.
- *Date of first picking.*—Oct. 2, 2006.
- *Date of last picking.*—Oct. 8, 2006.
- *Size.*—Average 3".
- *Form.*—Spherical.
- *Suture.*—Medium.
- *Weight.*—7.3–8 ounces.

Skin:
- *Thickness.*—Medium as compared to the species.
- *Texture.*—Medium as compared to the species.
- *Tendency to crack.*—None.
- *Down.*—Light (short as compared to the species).
- *Color.*—About 50–80% Dark Red (Pantone #195) over yellow ground color (Pantone #141).

Flesh:
- *Texture.*—Firm — non-melting, free of fiber.
- *Ripens.*—Evenly.
- *Flavor.*—Very good.
- *Aroma.*—Pleasant.
- *Eating quality.*—Excellent.
- *Brix.*—Average of 15%.
- *Color.*—Yellow (Pantone #142).
- *Pit cavity color.*—Red (Pantone #202).

Stone:

*Type.*—Freestone.

*Size.*—1¾" long — 1¼" wide — ¾" thick.

*Form.*—Ovate.

*Base.*—Straight.

*Apex.*—Pointed.

*Sides.*—Equal.

*Surface.*—Furrowed.

*Color.*—Reddish Brown (Pantone #187).

*Tendency to crack.*—None.

*Kernel.*—13/16" long — 9/16" wide — 3/16" thick.

*Kernel taste.*—Bland taste.

Use: Dessert.

Shipping quality: Very good.

Keeping quality: Very good (up to three (3) weeks).

Disease resistance: The fruit is resistance to brown rot.

The tree and its fruit herein described may vary slightly as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

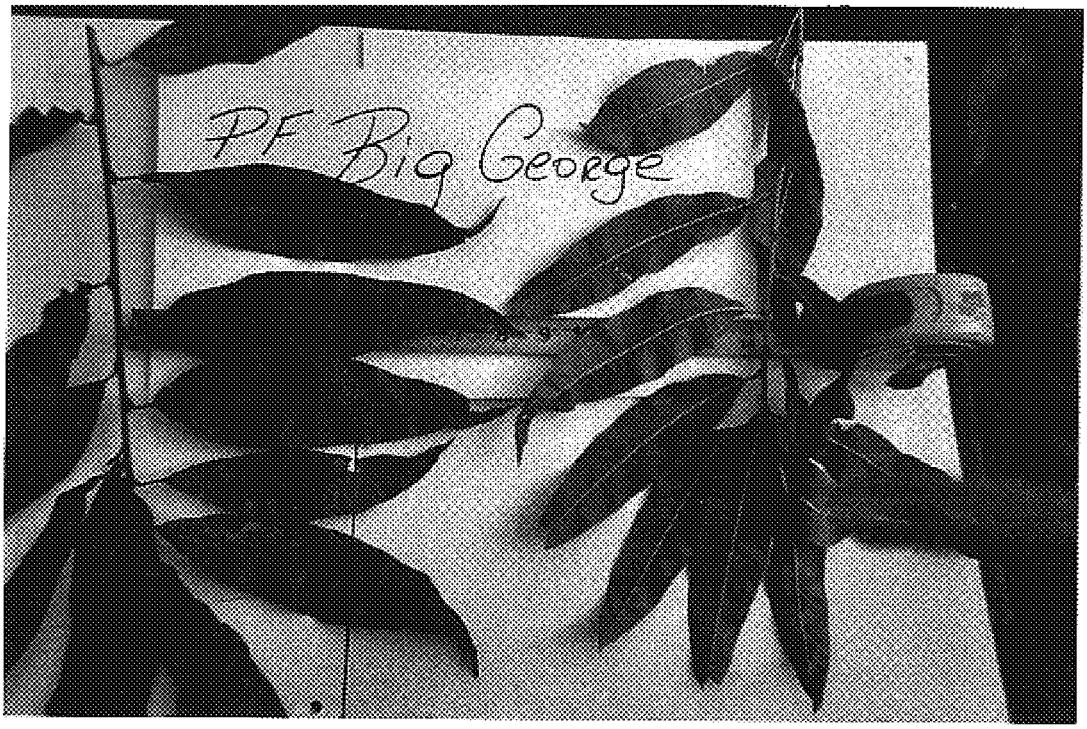
PF Big George
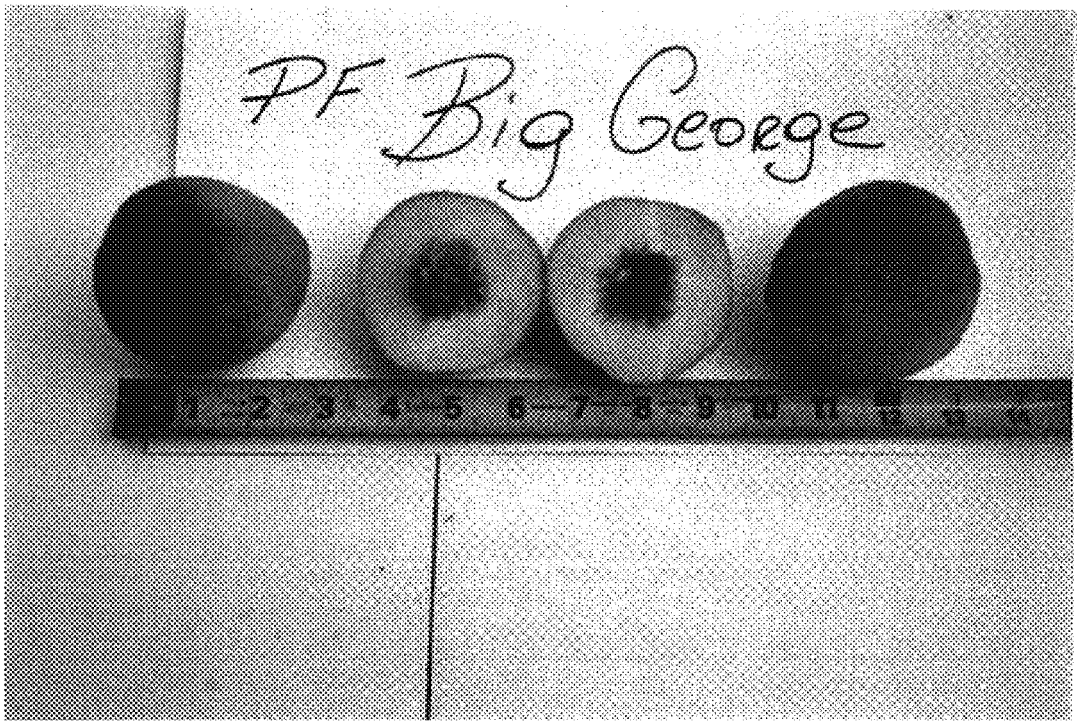
PF Big George